(12) United States Patent
Akbarali et al.

(10) Patent No.: US 9,809,551 B2
(45) Date of Patent: Nov. 7, 2017

(54) SOLID FORMS OF IVACAFTOR AND PROCESSES FOR THE PREPARATION THEREOF

(71) Applicant: Apotex Inc., Toronto (CA)

(72) Inventors: Padiyath Mohammed Akbarali, Bangalore (IN); Kintali Venkata Ramana, Bangalore (IN); Heggadde Nanjunda Bhatta Shreenivasa Murthy, Bangalore (IN); Sankaran Suresh Kumar, Tamil Nadu (IN); Ekkaluru Vijaya Bhaskar, Bangalore (IN); Nechipadappu Sunil Kumar, Bangalore (IN); Karad Manjunath, Bangalore (IN)

(73) Assignee: Apotex Inc., Toronto, Ontario (CA)

( * ) Notice: Subject to any disclaimer, the term of this patent is extended or adjusted under 35 U.S.C. 154(b) by 0 days.

(21) Appl. No.: 15/036,137

(22) PCT Filed: Nov. 13, 2014

(86) PCT No.: PCT/CA2014/000828
§ 371 (c)(1),
(2) Date: May 12, 2016

(87) PCT Pub. No.: WO2015/070336
PCT Pub. Date: May 21, 2015

(65) Prior Publication Data
US 2016/0280654 A1 Sep. 29, 2016

(30) Foreign Application Priority Data
Nov. 13, 2013 (IN) .......................... 5143/CHE/2013

(51) Int. Cl.
*C07D 215/56* (2006.01)
*A61K 31/47* (2006.01)
*A61P 11/00* (2006.01)

(52) U.S. Cl.
CPC ............ *C07D 215/56* (2013.01); *A61K 31/47* (2013.01); *C07B 2200/13* (2013.01)

(58) Field of Classification Search
CPC .............................. C07D 215/04; A61K 31/47
USPC .......................... 546/156; 514/312; 544/156
See application file for complete search history.

(56) References Cited

U.S. PATENT DOCUMENTS

| | | |
|---|---|---|
| 7,495,103 B2 | 2/2009 | Hadida-Ruah et al. |
| 8,163,772 B2 | 4/2012 | DeMattei et al. |
| 8,410,274 B2 | 4/2013 | Hurter et al. |
| 8,471,029 B2 | 6/2013 | Arekar et al. |
| 8,476,442 B2 | 7/2013 | DeMattei et al. |

FOREIGN PATENT DOCUMENTS

| | | |
|---|---|---|
| WO | 2013158121 A1 | 10/2013 |
| WO | 2014118805 A1 | 8/2014 |

OTHER PUBLICATIONS

Anonymous et al., "Crystalline Forms of N-(2,4-Di-Tert-Butyl-5-Hydroxyphenyl)-I,4-Hydr0-4-0xoquinoline-3-Carboxamide", IP.com Electronic Publication, Jan. 21, 2014, IP.com No. 000234586, 6 pages.
Zhang et al., "Dosable solvates of ivacaftor with high boiling point liquids", CrystEngComm, 2012, vol. 14, pp. 2422-2427.

*Primary Examiner* — Vankataraman Balasubramanian
(74) *Attorney, Agent, or Firm* — The Webb Law Firm

(57) ABSTRACT

Provided herein is a polymorphic form of Ivacaftor, namely APO-I, as well as processes for the preparation and pharmaceutical compositions of the same. Also, provided is a new solvate of Ivacaftor, processes for its preparation and use in the preparation of pure Ivacaftor.

9 Claims, 3 Drawing Sheets

SOLID FORMS OF IVACAFTOR AND PROCESSES FOR THE PREPARATION THEREOF

CROSS-REFERENCE TO RELATED APPLICATIONS

This application is the United States national phase of International Application No. PCT/CA2014/000828 filed Nov. 13, 2013, and claims priority to Indian Patent Application No. 5143/CHE/2013 filed Nov. 13, 2013, the disclosures of which are hereby incorporated in their entirety by reference.

TECHNICAL FIELD

This invention provides a new polymorphic form of Ivacaftor, as well as processes for the preparation and pharmaceutical compositions of the same. This invention also provides a new solvate of Ivacaftor and processes for the preparation thereof.

BACKGROUND

Ivacaftor (trade name Kalydeco™) is a potent and selective CFTR potentiator approved for the treatment of adult patients with G551D mutation of cystic fibrosis. Ivacaftor is chemically known as N-(2,4-di-tert-butyl-5-hydroxyphenyl)-1,4-dihydro-4-oxoquinoline-3-carboxamide and has the following structural formula:

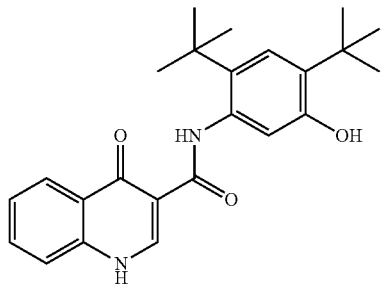 [SMILES: CC(C)(C)c1cc(C(C)(C)C)c(NC(=O)c2c[nH]c3ccccc3c2=O)cc1O]

U.S. Pat. No. 7,495,103 (hereinafter referred to as the '103 patent) relates to modulators of ATP-Binding Cassette ("ABC") transporters or fragments thereof, including Cystic Fibrosis Transmembrane Conductance Regulator, compositions thereof, and methods therewith. '103 also relates to methods of treating ABC transporter mediated diseases using such modulators.

U.S. Pat. No. 8,476,442 (hereinafter referred to as the '442 patent) provides a process for the preparation of a compound of Formula 1, comprising coupling a carboxylic acid of Formula 2 with an aniline of Formula 3 in the presence of a coupling agent.

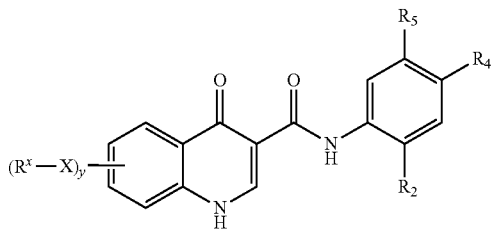

(1)

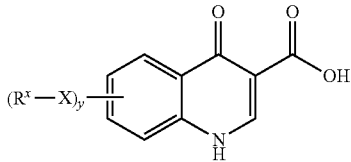

(2)

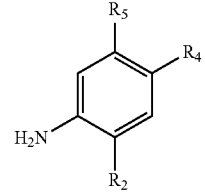

(3)

U.S. Pat. No. 8,163,772 discloses salts and co-solvates of N-[2,4-bis(1,1-dimethylethyl)-5-hydroxyphenyl]-1,4-dihydro-4-oxoquinoline-3-carboxamide, including crystalline forms thereof.

Zhang, et al., in *Cryst Eng Comm* (2012), 14(7), 2422-2427 describe an effort to create novel solvates of Ivacaftor, formed with 2-methylbutyric acid and isobutyric acid respectively, in pursuit of a more robust and reliable scale-up process. The solvates were characterized by X-ray crystallography, X-ray diffraction, differential scanning calorimetry, thermogravimetric analysis, and dynamic vapor sorption. The vapor sorption analysis showed the isobutyric acid solvate to be less stable than the 2-methylbutyric acid solvate, which became the focus of subsequent investigations. The 2-methylbutyric acid solvate was administered to rats and dogs in a series of pharmacokinetic studies, and showed excellent in vivo bioavailability. Thus, using liquid-state co-formers led to a solid form that is bioavailable, as well as stable and processable, suggesting that using such liquid-state co-formers could potentially benefit pharmaceutical development more broadly.

U.S. Pat. No. 8,410,274 relates to solid state forms of N-[2,4-bis(1,1-dimethylethyl)-5-hydroxyphenyl]-1,4-dihydro-4-oxoquinoline-3-carboxamide, pharmaceutical compositions thereof and methods therewith U.S. Pat. No. 8,471,029 relates to solid state forms of N-[2,4-bis(1,1-dimethylethyl)-5-hydroxyphenyl]-1,4-dihydro-4-oxoquinoline-3-carboxamide, pharmaceutical compositions thereof and methods therewith.

SUMMARY

The present invention relates, at least in part, to a polymorphic form of Ivacaftor, hereinafter termed as "polymorphic form APO-I of Ivacaftor", as well as processes for the preparation and pharmaceutical compositions of the same.

The present invention also relates, at least in part, to a solvate of Ivacaftor, which solvate is a methyl isobutyl ketone solvate of Ivacaftor, and processes for the preparation thereof.

The present invention also relates, at least in part, to a process for the preparation of pure Ivacaftor by using Ivacaftor solvates.

In illustrative embodiments, there is provided a polymorphic form APO-I of Ivacaftor characterized by a powder x-ray diffractogram comprising peaks, in terms of 2-theta degrees, at: 4.3±0.2, 4.8±0.2, 9.5±0.2, 13.0±0.2, 20.0±0.2 and 28.8±0.2.

In illustrative embodiments, there is provided a polymorphic form APO-I of Ivacaftor described herein wherein the powder x-ray diffractogram further comprises at least one peak, in terms of 2-theta degrees, selected from the group consisting of: 9.0±0.2, 12.0±0.2, 14.8±0.2, 16.1±0.2, 21.7±0.2 and 27.9±0.2.

In illustrative embodiments, there is provided a polymorphic form APO-I of Ivacaftor characterized by a powder x-ray diffractogram substantially similar to that shown in FIG. 1.

In illustrative embodiments, there is provided a polymorphic form APO-I of Ivacaftor described herein characterized by a DSC thermogram having endothermic peaks at about 240.8° C. and about 315.8° C. and an exothermic peak at about 245.9° C.

In illustrative embodiments, there is provided a polymorphic form APO-I of Ivacaftor described herein characterized by a DSC thermogram substantially similar to that shown in FIG. 2.

In illustrative embodiments, there is provided a process for the preparation of a polymorphic form APO-I of Ivacaftor, the process comprising: (a) adding an Ivacaftor solvate to an organic solvent or a mixture of organic solvents, thereby forming a reaction mixture; (b) maintaining the reaction mixture at a temperature range of from about 0° C. to about 60° C.; and (c) isolating the polymorphic form APO-I of Ivacaftor.

In illustrative embodiments, there is provided a process described herein wherein the Ivacaftor solvate is a solvate with methanol, ethanol, methyl ethyl ketone, isopropyl acetate, acetonitrile, methyl isobutyl ketone or water.

In illustrative embodiments, there is provided a process described herein wherein the Ivacaftor solvate is a methyl isobutyl ketone solvate of Ivacaftor.

In illustrative embodiments, there is provided a process described herein wherein the organic solvent is methanol, ethanol, propanol, isopropanol, butanol, toluene, xylene, hexane, heptane or a mixture thereof.

In illustrative embodiments, there is provided a process described herein wherein the organic solvent is a mixture of toluene and methanol.

In illustrative embodiments, there is provided a process described herein wherein the volume ratio of toluene to methanol in the mixture is in the range of from about 1 to 1 to about 1 to 10.

In illustrative embodiments, there is provided a process described herein wherein the volume ratio of toluene to methanol in the mixture is 1 to 1.

In illustrative embodiments, there is provided a process described herein wherein the temperature is in the range of from about 20° C. to about 30° C.

In illustrative embodiments, there is provided a pharmaceutical composition comprising the polymorphic form APO-I of Ivacaftor described herein with one or more pharmaceutically acceptable carriers.

In illustrative embodiments, there is provided a methyl isobutyl ketone solvate of Ivacaftor.

In illustrative embodiments, there is provided a methyl isobutyl ketone solvate of Ivacaftor described herein wherein the molar ratio of Ivacaftor to methyl isobutyl ketone is 1 to 1.

In illustrative embodiments, there is provided a methyl isobutyl ketone solvate of Ivacaftor described herein characterized by a powder x-ray diffractogram comprising peaks, in terms of 2-theta degrees, at: 4.4±0.2, 8.9±0.2, 11.8±0.2, 15.0±0.2, 15.5±0.2, 17.8±0.2 and 19.0±0.2.

In illustrative embodiments, there is provided a methyl isobutyl ketone solvate of Ivacaftor described herein wherein the powder x-ray diffractogram further comprises at least one peak, in terms of 2-theta degrees, selected from the group consisting of: 11.5±0.2, 13.3±0.2, 23.3±0.2 and 26.5±0.2.

In illustrative embodiments, there is provided a methyl isobutyl ketone solvate of Ivacaftor described herein characterized by a PXRD diffractogram substantially similar to that shown in FIG. 3.

In illustrative embodiments, there is provided a process for the preparation of methyl isobutyl ketone solvate of Ivacaftor, the process comprising: (i) reacting, in an organic solvent, 4-oxo-1,4-dihydroquinoline-3-carboxylic acid with 5-amino-2,4-di-tert-butylphenol or its acid addition salt, thereby forming a reaction mixture; (ii) adding methyl isobutyl ketone to the reaction mixture, thereby forming a solvated reaction mixture; and (iii) isolating methyl isobutyl ketone solvate of Ivacaftor.

In illustrative embodiments, there is provided a process described herein wherein methyl isobutyl ketone is added to the reaction mixture at a temperature in the range of from about 0° C. to about 60° C.

In illustrative embodiments, there is provided a process described herein process of claim 20 wherein methyl isobutyl ketone is added to the reaction mixture at a temperature in the range of from about 20° C. to about 30° C.

In illustrative embodiments, there is provided a process for the preparation of pure Ivacaftor, the process comprising: (I) reacting, in an organic solvent, 4-oxo-1,4-dihydroquinoline-3-carboxylic acid with 5-amino-2,4-di-tert-butylphenol or its acid addition salt, thereby forming a reaction mixture; (II) adding methyl isobutyl ketone to the reaction mixture, thereby forming a solvated reaction mixture; (III) isolating methyl isobutyl ketone solvate of Ivacaftor, thereby forming isolated methyl isobutyl ketone solvate of Ivacaftor; (IV) adding the isolated methyl isobutyl ketone solvate of Ivacaftor to a second organic solvent or a mixture of second organic solvents, thereby forming a second reaction mixture; (V) maintaining the second reaction mixture at a temperature in the range of from about 0° to about 60° C., thereby forming a maintained second reaction mixture; and (VI) isolating pure Ivacaftor.

In illustrative embodiments, there is provided a process described herein wherein methyl isobutyl ketone is added to the reaction mixture at a temperature in the range of from about 0° C. to about 60° C.

In illustrative embodiments, there is provided a process described herein wherein methyl isobutyl ketone is added to the reaction mixture at a temperature in the range of from about 20° C. to about 30° C.

In illustrative embodiments, there is provided a process described herein wherein second organic solvent is methanol, ethanol, propanol, isopropanol, butanol, toluene, xylene, hexane, heptane or a mixture thereof.

In illustrative embodiments, there is provided a process described herein wherein the second organic solvent is a mixture of toluene and methanol.

In illustrative embodiments, there is provided a process described herein wherein the second reaction mixture is maintained at a temperature in the range of from about 20° C. to about 30° C.

In illustrative embodiments, there is provided use of a solvate of Ivacaftor in the preparation of pure Ivacaftor.

In illustrative embodiments, there is provided a use described herein wherein the solvate of Ivacaftor is a methyl isobutyl ketone solvate of Ivacaftor.

Other aspects and features of the present invention will become apparent to those ordinarily skilled in the art upon review of the following description of specific embodiments of the invention in conjunction with the accompanying figures.

DETAILED DESCRIPTION

When used in reference to a diffractogram, a spectrum and/or data presented in a graph, the term "substantially similar" means that the subject diffractogram, spectrum and/or data presented in the graph encompasses all diffractograms, spectra and/or data presented in graphs that vary within the acceptable boundaries of experimentation that are known to a person of skill in the art. Such boundaries of experimentation will vary depending on the type of the subject diffractogram; spectrum and/or data presented in a graph, and are known to and understood by a person of skill in the art.

When used in reference to a peak in a powder X-ray diffraction (PXRD) diffractogram, the term "about" means that the peak may vary by ±0.2 2-theta degrees of the subject value.

When used in reference to a peak in the DSC thermogram, the term "about" means that the peak may vary by ±1 degrees centigrade of the subject value.

As used herein when referring to a diffractogram, spectrum and/or to data presented in a graph, the term "peak" refers to a feature that one skilled in the art would recognize as not attributing to background noise.

Depending on the nature of the methodology applied and the scale selected to display results obtained from an X-ray diffraction analysis, an intensity of a peak obtained may vary quite dramatically. For example, it is possible to obtain a relative peak intensity of 0.01% when analysing one sample of a substance, but another sample of the same substance may show a much different relative intensity for a peak at the same position. This may be due, in part, to the preferred orientation of the sample and its deviation from the ideal random sample orientation, sample preparation and the methodology applied. Such variations are known and understood by a person of skill in the art.

As used herein, the term pure Ivacaftor refers to Ivacaftor that may be at least about 98%, or at least about 99.5%, or at least about 99.9% pure and correspondingly the level of impurities may be less than about 2%, or less than about 0.5%, or at least about 0.1% by weight as determined by high performance liquid chromatography (HPLC).

This invention provides a polymorphic form APO-I of Ivacaftor. In some embodiments, it may be characterized by having a powder x-ray diffractogram (PXRD) comprising peaks, in terms of 2-theta degrees, at: about 4.3, about 4.8, about 9.5, about 13.0, about 20.0 and about 28.8.

In some embodiments, the polymorphic form APO-I of Ivacaftor may be characterized by having a PXRD further comprising at least one peak, in terms of 2-theta degrees, selected from the group consisting of: about 9.0, about 12.0, about 14.8, about 16.1, about 21.7 and about 27.9.

Figure 1:
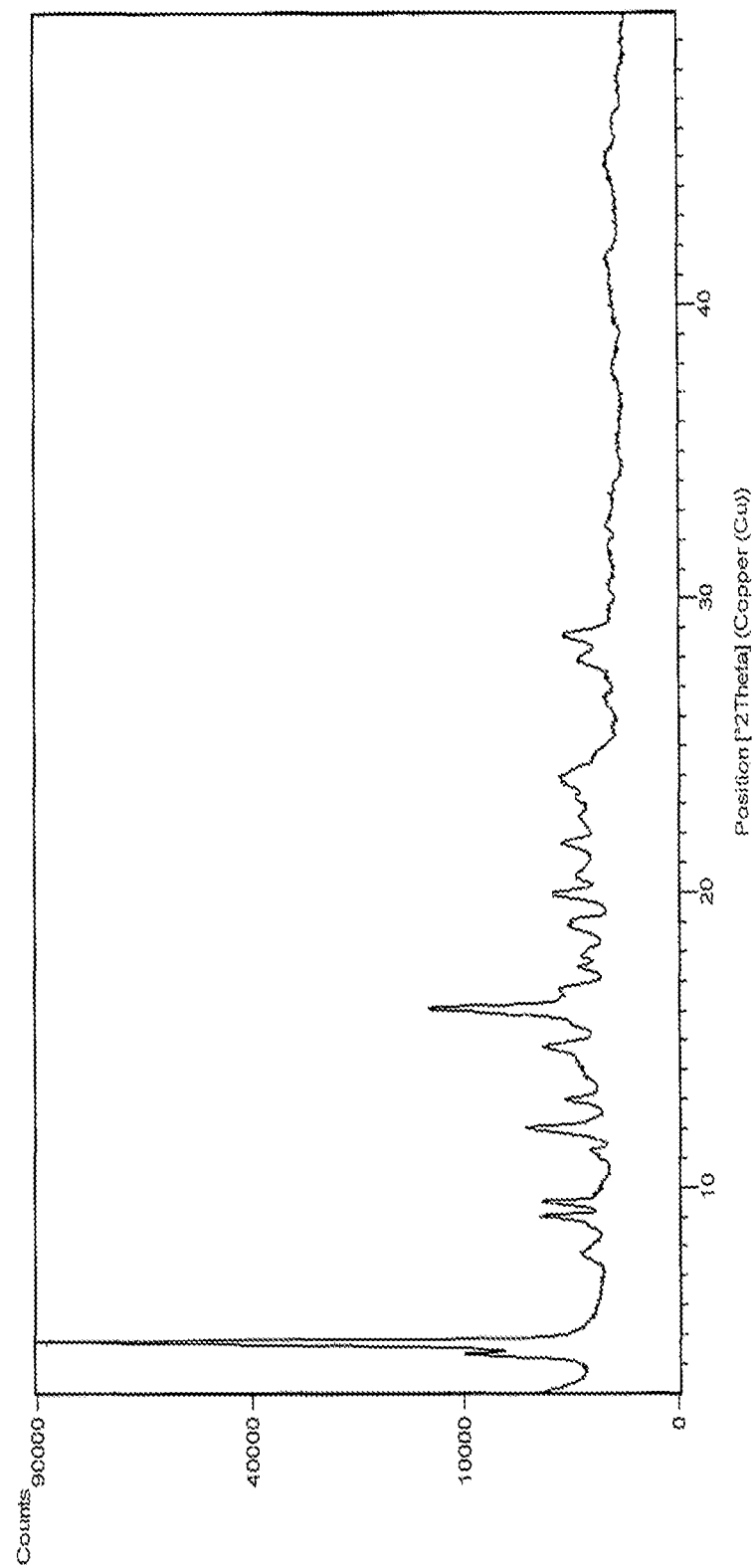
FIG. 1 is a characteristic powder X-ray diffraction (PXRD) diffractogram of the polymorphic form APO-I of Ivacaftor.

In some embodiments, the polymorphic form APO-I of Ivacaftor may be characterized by a PXRD diffractogram substantially similar to that shown in FIG. 1.

In some embodiments, the polymorphic form APO-I of Ivacaftor may be characterized by the following PXRD peaks as shown in Table 1, ±0.2 2-theta degrees:

TABLE 1

| Diffraction angles (2-theta°) | d-spacing (A°) | Rel. Intensity (I/I₀ %) |
| --- | --- | --- |
| 4.34 | 20.33 | 9.49 |
| 4.78 | 18.47 | 100.00 |
| 7.67 | 11.52 | 0.79 |
| 9.03 | 9.78 | 3.13 |
| 9.52 | 9.28 | 3.10 |
| 11.27 | 7.85 | 0.58 |
| 12.05 | 7.34 | 4.17 |
| 13.00 | 6.80 | 1.77 |
| 13.78 | 6.42 | 0.40 |
| 14.77 | 5.99 | 2.70 |
| 15.51 | 5.71 | 1.01 |
| 16.09 | 5.50 | 14.01 |
| 16.77 | 5.28 | 1.79 |
| 17.47 | 5.07 | 0.93 |
| 17.85 | 4.96 | 0.81 |
| 18.11 | 4.89 | 0.50 |
| 18.82 | 4.71 | 1.46 |
| 19.07 | 4.65 | 1.44 |
| 20.00 | 4.43 | 2.13 |
| 20.56 | 4.31 | 0.78 |
| 21.65 | 4.10 | 1.42 |
| 22.59 | 3.93 | 0.41 |
| 23.21 | 3.83 | 0.65 |
| 23.93 | 3.71 | 1.72 |
| 26.72 | 3.33 | 0.18 |
| 27.92 | 3.19 | 1.22 |
| 28.82 | 3.09 | 1.90 |
| 30.37 | 2.94 | 0.15 |
| 31.87 | 2.80 | 0.15 |
| 32.48 | 2.75 | 0.25 |
| 33.74 | 2.65 | 0.10 |
| 35.35 | 2.53 | 0.03 |
| 37.81 | 2.37 | 0.15 |
| 39.54 | 2.27 | 0.03 |
| 41.65 | 2.16 | 0.19 |
| 44.94 | 2.01 | 0.19 |
| 46.40 | 1.95 | 0.15 |
| 47.82 | 1.90 | 0.08 |

Figure 2:
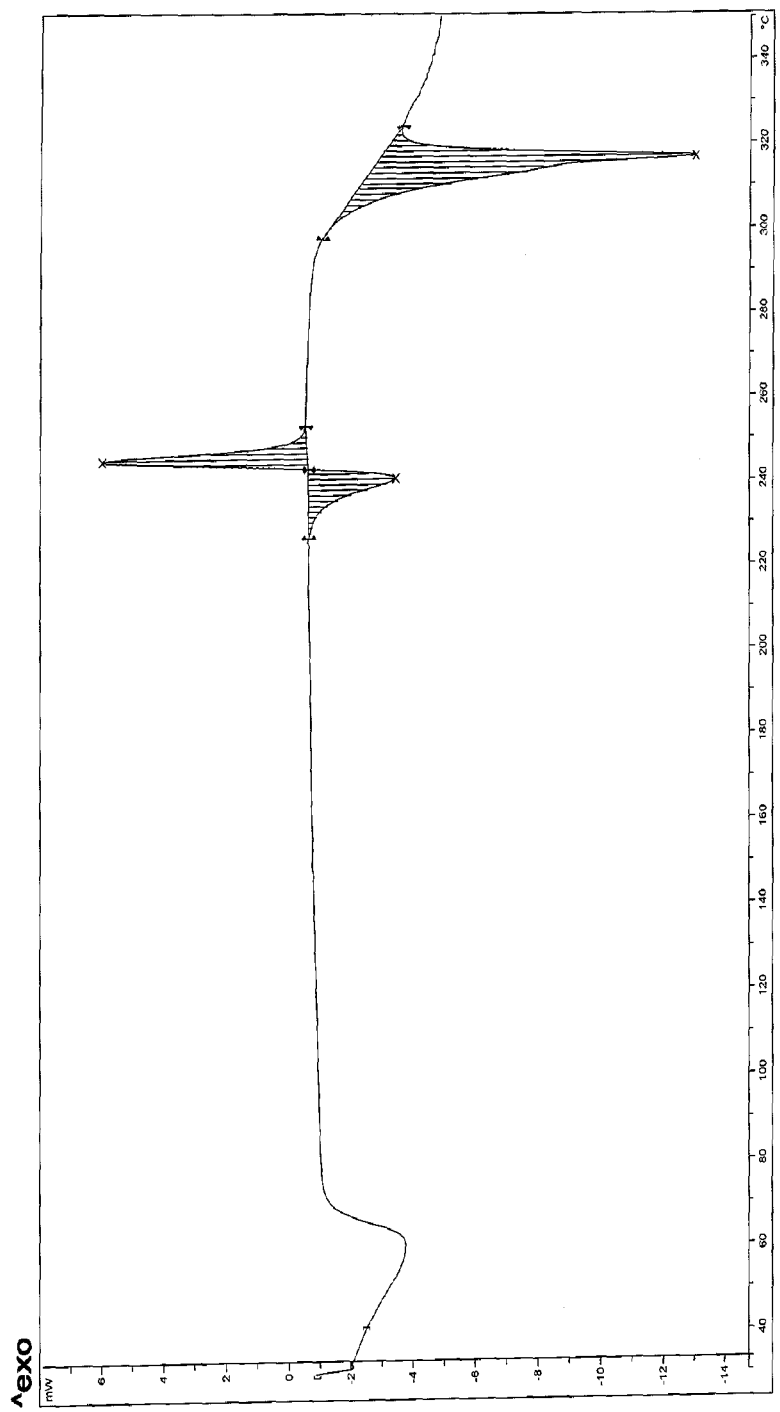
FIG. 2 is a characteristic differential scanning calorimetry (DSC) thermogram of the polymorphic form APO-I of Ivacaftor.

In some embodiments, the polymorphic form APO-I of Ivacaftor may be characterized by a differential scanning calorimetry (DSC) thermogram substantially similar to that shown in FIG. 2.

In some embodiments, the polymorphic form APO-I of Ivacaftor may be characterized by a differential scanning calorimetry (DSC) thermogram comprising two endothermic peaks at about 240.8° C. and about 315.8° C. and an exothermic peak at about 245.9° C.

This invention also provides methyl isobutyl ketone solvate of Ivacaftor. The molar ratio of Ivacaftor to methyl isobutyl ketone in a preferred embodiment is 1 to 1.

In some embodiments, methyl isobutyl ketone solvate of Ivacaftor may be characterized by having a PXRD comprising peaks, in terms of 2-theta degrees at: about 4.4, about 8.9, about 11.8, about 15.0, about 15.5, about 17.8 and about 19.0.

In some embodiments, methyl isobutyl ketone solvate of Ivacaftor may be characterized by having a PXRD further comprising at least one peak, in terms of 2-theta degrees, selected from the group consisting of: about 11.5, about 13.3, about 23.3 and about 26.5.

Figure 3:
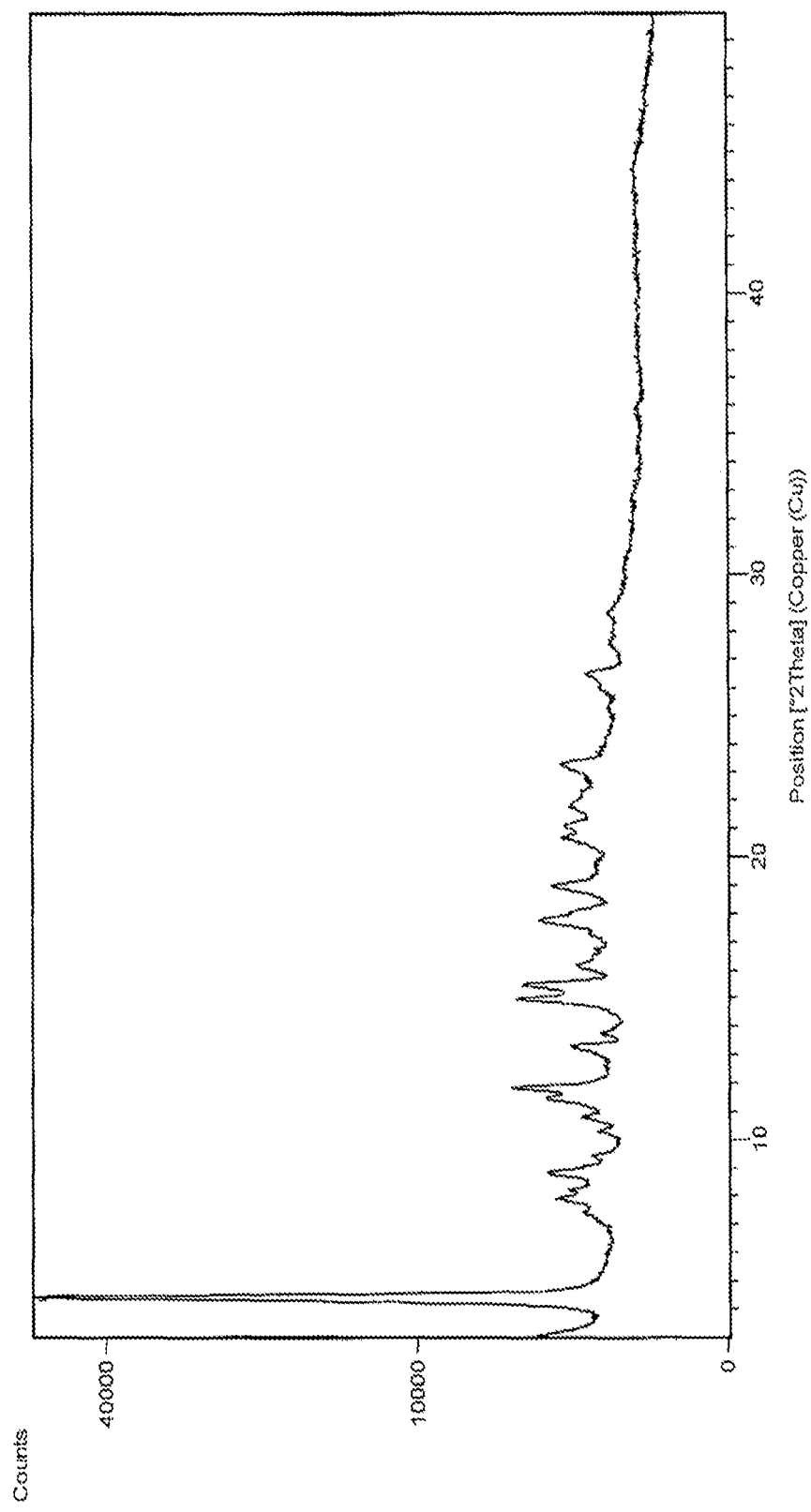
FIG. 3 is a characteristic powder X-ray diffraction (PXRD) diffractogram of methyl isobutyl ketone solvate of Ivacaftor.

In some embodiments, methyl isobutyl ketone solvate of Ivacaftor may be characterized by a PXRD diffractogram substantially similar to that shown in FIG. 3.

In some embodiments, methyl isobutyl ketone solvate of Ivacaftor may be characterized by the following PXRD peaks as shown in Table 2, ±0.2 2-theta degrees:

TABLE 2

| Diffraction angles (2-theta°) | d-spacing (A°) | Rel. Intensity (I/I₀ %) |
|---|---|---|
| 4.44 | 19.89 | 100.00 |
| 7.40 | 11.93 | 1.51 |
| 7.95 | 11.11 | 3.19 |
| 8.22 | 10.74 | 2.65 |
| 8.85 | 9.98 | 4.10 |
| 9.43 | 9.37 | 1.20 |
| 10.26 | 8.61 | 1.01 |
| 10.77 | 8.20 | 1.84 |
| 11.51 | 7.68 | 4.46 |
| 11.84 | 7.47 | 7.47 |
| 13.32 | 6.64 | 2.74 |
| 13.78 | 6.42 | 1.02 |
| 14.98 | 5.91 | 7.00 |
| 15.54 | 5.70 | 5.71 |
| 16.12 | 5.49 | 1.90 |
| 17.23 | 5.14 | 0.82 |
| 17.75 | 4.99 | 4.22 |
| 19.00 | 4.66 | 2.85 |
| 20.68 | 4.29 | 2.22 |
| 21.08 | 4.21 | 2.25 |
| 21.80 | 4.07 | 1.87 |
| 23.29 | 3.81 | 2.73 |
| 26.48 | 3.36 | 1.41 |
| 27.55 | 3.23 | 0.31 |
| 28.64 | 3.11 | 0.51 |
| 30.37 | 2.94 | 0.14 |
| 32.74 | 2.73 | 0.11 |
| 35.99 | 2.49 | 0.11 |

Another aspect of this invention is a process for the preparation of the polymorphic form APO-I of Ivacaftor, the process comprising:
(a) adding an Ivacaftor solvate to an organic solvent or a mixture of organic solvents, thereby forming a reaction mixture;
(b) maintaining the reaction mixture at a temperature range of from 0° C. to 60° C.; and
(c) isolating the polymorphic form APO-I of Ivacaftor.

In some embodiments of step (a), the solvate of Ivacaftor may be a solvate with methanol, ethanol, methyl ethyl ketone, isopropyl acetate, acetonitrile, methyl isobutyl ketone and water (hydrate). In a preferred embodiment of step (a), the Ivacaftor solvate is methyl isobutyl ketone solvate of Ivacaftor.

In some embodiments of step (a), an Ivacaftor solvate is added to a polar or non-polar organic solvent or a mixture thereof. A polar organic solvent may be methanol, ethanol, propanol, isopropanol or butanol, preferably methanol. A non-polar organic solvent may be toluene, xylene, hexane or heptane, preferably toluene. Where a mixture of solvents is used, the volume by volume ratio of solvents may vary in the range of from about 1 to 1 to about 1 to 10.

In some embodiments of step (a), an Ivacaftor solvate is added to an organic solvent or a mixture thereof at the temperature range of from 0° C. to 60° C., preferably in the range of from about 10° C. to about 30° C., more preferably in the range from about 20° C. to about 30° C.

In some embodiments of step (b), the reaction mixture is maintained for a period of 10 minutes to 5 hours at the temperature range of from 0° C. to 60° C., preferably in the range of from about 10° C. to about 30° C., more preferably in the range of from about 20° C. to about 30° C.

In some embodiments of step (c), the polymorphic form APO-I of Ivacaftor is isolated from the reaction mixture by one or more of the conventional techniques such as filtration, suction filtration, concentration, decantation, centrifugation, gravity filtration, and other techniques known to a person of skill in the art.

In some embodiments, the isolated polymorphic form APO-I of Ivacaftor may be dried at a temperature in the range of from about 30° C. to 60° C., preferably in the range of from about 40° C. to 50° C. under vacuum. Drying may be carried out under reduced pressure until the residual solvent reduces to a desired amount such as an amount within the limits given by the International Conference on Harmonization of Technical Requirements for Registration of Pharmaceuticals for Human Use (ICH) guidelines. The choice of temperatures and pressures for drying depends on the volatility of a solvent or solvents in use. Drying of the isolated polymorphic form APO-I of Ivacaftor may be carried out by a method known in the art including a tray dryer, vacuum oven, air oven, or using a fluidized bed drier, spin flash dryer, flash dryer, and the like.

Another aspect of this invention provides a process for the preparation of methyl isobutyl ketone solvate of Ivacaftor, the process comprising:
(i) reacting, in an organic solvent, 4-oxo-1,4-dihydroquinoline-3-carboxylic acid with 5-amino-2,4-di-tert-butylphenol or its acid addition salt, thereby forming a reaction mixture;
(ii) adding methyl isobutyl ketone to the reaction mixture, thereby forming a solvated reaction mixture; and
(iii) isolating methyl isobutyl ketone solvate of Ivacaftor.

In some embodiments of step (i), the 5-amino-2,4-di-tert-butylphenol may be used in its free form or as any one of its acid addition salts, including hydrochloride, hydrobromide, acetate, tosylate or besylate, preferably hydrochloride. In some embodiments of step (i), the reaction may be carried out in the presence of a coupling agent, including N,N,N',N'-tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxid hexafluorophosphate (HATU), (benzotriazol-1-yl-oxy)-tris(dimethylamino)phosphonium hexafluorophosphate (BOP), pentafluorophenyl trifluoroacetate (PFP-TFA) or 2-propane phosphonic anhydride ($T_3P$), preferably HBTU. In some embodiments of step (i), the reaction is carried out at a temperature in the range of from about 0° C. to 60° C., preferably in the range of from about 10° C. to about 40° C., and more preferably in the range of from about 20° C. to about 30° C.

In some embodiments of step (ii), methyl isobutyl ketone is added to the reaction mixture at a temperature in the range of from about 0° C. to 60° C., preferably in the range of from about 10° C. to about 40° C., and more preferably in the range of from about 20° C. to about 30° C.

In some embodiments of step (iii), methyl isobutyl ketone solvate of Ivacaftor is isolated from the reaction mixture by one or more of the conventional techniques such as filtration, suction filtration, concentration, decantation, centrifugation, gravity filtration, and other techniques known to a person of skill in the art.

In some embodiments, the isolated methyl isobutyl ketone solvate of Ivacaftor may be dried at a temperature in the range of from 30° C. to 60° C., preferably in the range of from about 40° C. to 50° C. under vacuum. Drying may be carried out under reduced pressure until the residual solvent reduces to the desired amount such as an amount within the limits given by International Conference on Harmonization of Technical Requirements for Registration of Pharmaceuticals for Human Use (ICH) guidelines. The choice of temperatures and pressures for drying depends on the volatility of a solvent or solvents in use. Drying of the isolated methyl isobutyl ketone solvate of Ivacaftor may be carried out by a method known in the art including a tray dryer, vacuum oven, air oven, or using a fluidized bed drier, spin flash dryer, flash dryer.

Another aspect of this invention is a use of a solvate of Ivacaftor in the preparation of pure Ivacaftor. One embodiment uses methyl isobutyl ketone solvate of Ivacaftor in the preparation of pure Ivacaftor. Another aspect of this invention provides a process for the preparation of pure Ivacaftor from an Ivacaftor solvate, particularly methyl isobutyl ketone solvate of Ivacaftor.

Another aspect of the present invention provides a process for the preparation of pure Ivacaftor, the process comprising:
(I) reacting, in an organic solvent, 4-oxo-1,4-dihydroquinoline-3-carboxylic acid with 5-amino-2,4-di-tert-butylphenol or its acid addition salt, thereby forming a reaction mixture;
(II) adding methyl isobutyl ketone to the reaction mixture, thereby forming a solvated reaction mixture;
(III) isolating methyl isobutyl ketone solvate of Ivacaftor, thereby forming isolated methyl isobutyl ketone solvate of Ivacaftor;
(IV) adding the isolated methyl isobutyl ketone solvate of Ivacaftor to a second organic solvent or a mixture of second organic solvents, thereby forming a second reaction mixture;
(V) maintaining the second reaction mixture at a temperature in the range of from 0° C. to 60° C., thereby forming a maintained second reaction mixture; and
(VI) isolating pure Ivacaftor.

In some embodiments of step (I), 5-amino-2,4-di-tert-butylphenol may be used in its free form or as any one of its acid addition salts, including hydrochloride, hydrobromide, acetate, tosylate or besylate, preferably hydrochloride. In some embodiments of step (I), the reaction may be carried out in the presence of a coupling agent, including N,N,N',N'-tetramethyl-O-(1H-benzotriazol-1-yl)uronium hexafluorophosphate (HBTU), 1-[bis(dimethylamino)methylene]-1H-1,2,3-triazolo[4,5-b]pyridinium 3-oxid hexafluorophosphate (HATU), (benzotriazol-1-yl-oxy)-tris(dimethylamino)phosphonium hexafluorophosphate (BOP), pentafluorophenyl trifluoroacetate (PFP-TFA) or 2-propane phosphonic anhydride ($T_3P$), preferably HBTU, In some embodiments of step (a), the reaction is carried out at a temperature in the range of from about 0° C. to 60° C., preferably in the range of from about 10° C. to about 40° C., and more preferably in the range of from about 20° C. to about 30° C.

In some embodiments of step (II), methyl isobutyl ketone is added to the reaction mixture at a temperature in the range of from 0° C. to 60° C., preferably in the range of from 10° C. to 40° C., and more preferably in the range of from 20° C. to 30° C.

In some embodiments of step (III), methyl isobutyl ketone solvate of Ivacaftor is isolated from the solvated reaction mixture by one or more of the conventional techniques such as filtration, suction filtration, concentration, decantation, centrifugation, gravity filtration, and other techniques known to a person of skill in the art.

In some embodiments of step (III), methyl isobutyl ketone solvate of Ivacaftor may be dried. Drying of the isolated methyl isobutyl ketone solvate of Ivacaftor can be carried out at a temperature in the range of from about 30° C. to 60° C., preferably in the range of from about 40° C. to 50° C. under vacuum for about 1 to 20 hours. The choice of temperatures and pressures for drying depends on the volatility of a solvent or solvents in use. Drying of the isolated methyl isobutyl ketone solvate of Ivacaftor may be carried out by a method known in the art including a tray dryer, vacuum oven, air oven, or using a fluidized bed drier, spin flash dryer, flash dryer, and the like.

In some embodiments of step (IV), methyl isobutyl ketone solvate of Ivacaftor is added to a polar or non-polar organic solvent or a mixture thereof. The polar organic solvent may be methanol, ethanol, propanol, isopropanol or butanol, preferably methanol. The non-polar organic solvent may be toluene, xylene, hexane or heptane, preferably toluene. Where a mixture of solvents is used, the volume by volume ratio of solvents may vary from about 1 to 1 to about 1 to 10.

In some embodiments of step (IV), methyl isobutyl ketone solvate of Ivacaftor is added to the second organic solvent or the mixture of second organic solvents at a temperature in the range of from about 0° C. to 60° C. , preferably in the range of from about 10° C. to about 30° C., and more preferably in the range of from about 20° C. to about 30° C.

In some embodiments of step (V), the second reaction mixture is maintained for a period of 10 minutes to 3 hours at a temperature in the range of from 0° C. to 60° C., preferably in the range of from about 10° C. to about 30° C., more preferably in the range of from about 20° C. to about 30° C.

In some embodiments of step (VI), pure Ivacaftor may be isolated by one or more of the conventional techniques such as filtration, suction filtration, concentration, decantation, centrifugation, gravity filtration, and other techniques known to a person of skill in the art.

In some embodiments of step (VI), the isolated pure Ivacaftor may be dried at a temperature in the range of from about 30° C. to about 60° C., preferably in the range of from about 40° C. to about 50° C. under vacuum for about 1 to 20 hours. The choice of temperatures and pressures for drying depends on the volatility of a solvent or solvents in use and therefore the foregoing should be considered as only a general guidance. Drying of the isolated pure Ivacaftor may be carried out by a method known in the art including a tray dryer, vacuum oven, air oven, or using a fluidized bed drier, spin flash dryer, flash dryer, and the like.

In another aspect of the invention, the polymorphic form APO-I of Ivacaftor and/or pure Ivacaftor described herein may be used alone or in combination with one or more of the active pharmaceutical ingredients in the preparation of pharmaceutical compositions together with one or more of the pharmaceutically acceptable excipients, carriers or diluents. These pharmaceutical compositions may be formulated as follows: solid oral dosage forms including powders, granules, pellets, tablets, and capsules; liquid oral dosage forms including syrups, suspensions, dispersions, and emulsions; and injectable preparations including solutions, dispersions, and freeze dried compositions. These formulations may be in the form of immediate release, delayed release or modified release. Further, the immediate release compositions may be conventional, dispersible, chewable, mouth dissolving, or flash melt preparations. The modified release compositions may comprise hydrophilic or hydrophobic substances, or combinations of hydrophilic and hydrophobic substances, release rate controlling substances forming matrix or reservoir systems or combinations of matrix and reservoir systems. These compositions may be prepared by direct blending, dry granulation, or wet granulation or by extrusion and spheronization. These compositions may be presented as uncoated, film coated, sugar coated, powder coated, enteric coated or modified release coated.

Pharmaceutically acceptable excipients that may be used in making pharmaceutical dosage forms with the polymorphic form APO-I of Ivacaftor and/or pure Ivacaftor include diluents such as starch, pregelatinized starch, lactose, powdered cellulose, microcrystalline cellulose, dicalcium phosphate, tricalcium phosphate, mannitol, sorbitol, sugar, and the like; binders such as acacia, guar gum, tragacanth, gelatin, polyvinylpyrrolidones, hydroxypropyl celluloses, hydroxypropyl methylcelluloses, pregelatinized starches, and the like; disintegrants such as starch, sodium starch glycolate, pregelatinized starch, crospovidones, croscarmellose sodium, colloidal silicon dioxide, and the like; lubricants such as stearic acid, magnesium stearate, zinc stearate, and the like; glidants such as colloidal silicon dioxide and the like; solubility or wetting enhancers such as anionic, cationic, and neutral surfactants; complex forming agents such as various grades of cyclodextrins and resins; release rate controlling agents such as hydroxypropyl celluloses, hydroxymethyl celluloses, hydroxypropyl methylcelluloses, ethyl celluloses, methylcelluloses, various grades of methyl methacrylates, waxes, and the like. Other pharmaceutically acceptable excipients that may be used with the polymorphic form APO-I of Ivacaftor and/or pure Ivacaftor include, but are not limited to, film formers, plasticizers, colorants, flavoring agents, sweeteners, viscosity enhancers, preservatives, antioxidants, and the like.

These pharmaceutical compositions may be useful for treatment of cystic fibrosis.

EXAMPLES

The following examples demonstrate and further illustrate certain preferred embodiments and aspects of this invention. These examples are not to be construed as limiting the scope of this invention.

Instrumentation

The powder X-ray diffraction (PXRD) analysis reported herein was acquired on a PAN analytical X-pert Pro MPD diffractometer with fixed divergence slits and an X-Celerator RTMS detector. The diffractometer was configured in Bragg-Brentano geometry; data was collected over a 2-theta degree range of from 5 to 35 using CuK-alpha radiation at a power of 40 mA and 45 kV. CuK-beta radiation was removed using a divergent beam Nickel filter. A step size of 0.017 degrees was used. A step time of 20 seconds was used. Samples were rotated at 1 Hz to reduce preferred orientation effects. The samples were prepared by the back-loading technique.

The DSC thermogram reported herein was recorded on a Mettler-Toledo 822e instrument. Samples (1 to 3 mg) were weighed into a 40 μL aluminium pan and were crimped closed with an aluminium lid. The samples were analysed under a flow of nitrogen (ca. 50 mL/min) at a scan rate of 20° C. per minute, from 30° C. to 350° C.

The $^1$H NMR spectra were recorded on a Bruker 300 MHz instrument. The sample (5-10 mg) was dissolved in a deuterated solvent and the spectrum was recorded in the 0 to 15 ppm range.

The $^{13}$C NMR spectra were recorded on a Bruker 300 MHz instrument at a field of 75 MHz. The sample (5-10 mg) was dissolved in a deuterated solvent and the spectrum was recorded in the 0 to 250 ppm range.

The raw materials, 4-oxo-1,4-dihydroquinoline-3-carboxylic acid and 5-amino-2,4-di-tert-butylphenol hydrochloride, used in the following examples are commercially available or can be prepared using processes known in the art.

Example 1

Preparation of Methyl Isobutyl Ketone Solvate of Ivacaftor:
4-oxo-1,4-dihydroquinoline-3-carboxylic acid (22.45 g) in dimethyl formamide (125 mL) was added to a round bottomed flask fitted with a temperature inlet. N,N,N',N'-tetramethyl-O-(1H-benzotriazol-1-yl)uronium hexafluorophosphate (53.55 g) was further added to the reaction flask, forming a reaction mixture. The reaction mixture was stirred for 10 minutes at 20° C. to 30° C. 5-amino-2,4-di-tert-butylphenol hydrochloride (25.0 g) was added to the reaction mixture, followed by the addition of diisopropylethylamine (43.48 g). The reaction mass thus formed was stirred for 10 hours at 25° C. After completion of this reaction, methyl isobutyl ketone (500 mL) and 10% aqueous hydrochloric acid (125 mL) were both added to the reaction mixture and the reaction mixture was stirred for 10 minutes at 25° C. The resulting layers were separated. The organic layer was washed with 10% aqueous hydrochloric acid, then washed further with sodium carbonate solution followed by washing with water. The organic layer was distilled under vacuum up to the volume of 125 mL and the suspension was allowed to cool to a temperature of 25° C. The suspension was further cooled to 0° C. to 5° C. and stirred for one hour. The precipitated material was filtered and dried under vacuum at 50° C. for 10 hours.

Analysis:
$^1$H NMR (DMSO-d6, 300 MHz) delta-scale (ppm):
12.89-12.87 (d, 1H), 11.84 (s, 1H), 9.21 (s, 1H), 8.90-8.87 (d, 1H), 8.36-8.34 (d, 1H), 7.81-7.50 (m, 3H), 7.19 (s, 1H), 7.14 (s, 1H), 2.30-2.28 (d, 2H), 2.06 (s, 3H), 2.05-1.96 (m, 1H), 1.40 (s, 9H), 1.38 (s, 9H), 0.86-0.84 (d, 6H).

$^{13}$C NMR (DMSO-d6, 75MHz) delta-scale (ppm):
208.02, 176.38, 162.80, 153.25, 144.07, 139.12, 133.52, 132.82, 132.20, 131.52, 126.01, 125.54, 125.04, 123.70, 119.05, 115.96, 110.93, 51.76, 34.28, 33.92, 30.56, 29.99, 29.39, 23.85, 22.25.

Gas Chromatography: Methyl isobutyl content by gas chromatography: 24.7%.

PXRD: The PXRD diffractogram is shown in FIG. 3.

Example 2

Preparation of APO-I Ivacaftor:
Methyl isobutyl ketone solvate of Ivacaftor prepared in Example 1 was added to a mixture of methanol (50 mL) and toluene (50 mL) in a round bottom flask equipped with a mechanical stirrer, thermo pocket, guard tube and stopper. The reaction mixture was stirred at 20° C. to 30° C. for 1 hour. The material was filtered and washed with a mixture of methanol and toluene. The material was dried at 50° C. under vacuum.
Yield: 5.63 g.
Purity: 99.9% (by HPLC).
Analysis:
PXRD: The PXRD diffractogram is shown in FIG. 1.
DSC: The DSC thermogram is shown in FIG. 2.

Example 3

Preparation of Pure Ivacaftor:

4-oxo-1,4-dihydroquinoline-3-carboxylic acid (44.4 g) in dimethyl formamide (275 mL) was added to a round bottomed flask fitted with a temperature inlet. N,N,N',N'-tetramethyl-O-(1H-benzotriazol-1-yl)uronium hexafluorophosphate (101.1 g) was added to the reaction flask and the reaction mixture was stirred for 15 minutes at 25° C. 5-amino-2,4-di-tert-butylphenol hydrochloride (55.0 g) was added to the reaction mixture followed by the addition of diisopropylethylamine (82.7 g). The reaction mass was stirred for 2.5 hours at 45-50° C. After the completion of the reaction, methyl isobutyl ketone (550 mL) and 10% aqueous hydrochloric acid (275 mL) were added to the reaction mixture and stirred for 15 minutes at 25-30° C. The resulting layers were separated. The organic layer was washed with 15% aqueous hydrochloric acid (3×275 mL) and further washed with 10% aqueous sodium carbonate solution (2×275 mL), followed by washing with water (275 mL). The organic layer was distilled under vacuum up to the volume of 275 mL and the suspension was allowed to cool to a temperature of 25° C. The suspension was further cooled to 0-5° C. and stirred for 2 hours. The precipitated material was filtered and dried under vacuum at 45° C. for 8 hours.

Yield: 95.1 g

Methyl isobutyl ketone solvate of Ivacaftor (90 g) prepared above was added to a mixture of methanol (247.5 mL) and toluene (247.5 mL) in a round bottom flask equipped with mechanical stirrer, thermo pocket, guard tube and stopper. The reaction mixture was maintained under stirring at 25-30° C. for 2 hours. The material was filtered and washed with a mixture of methanol (90 mL) and toluene (90 mL). The material was dried at 70° C. under vacuum.

Yield: 57.5 g.

Purity: 100% (by HPLC).

Example 4

Ivacaftor APO-I polymorph samples were packed in an inner antistatic polyethylene bag sealed with a cable tie encased within a heat sealed composite aluminum out bag under nitrogen within a HDPE drum.

The samples were then tested for stability after storing at 25±2° C. with 60%±5% relative humidity (RH). Impurities, drug concentrations, polymorph stability and other parameters were measured at intervals during the storage.

The results of testing are presented in Table 3.

TABLE 3

| | | | Analytical data | |
|---|---|---|---|---|
| Condition | Time Period | Description | Assay (by HPLC) | XRPD |
| 25 ± 2° C. & 60 ± 5% RH | Initial | Off white Powder | 99.1% | APO-I Polymorph |
| | 12 months | Off white Powder | 99.8% | Complies with APO-I Polymorph |

What is claimed is:

1. A polymorphic form APO-I of Ivacaftor having a powder x-ray diffractogram comprising peaks, in terms of 2-theta degrees, at: 4.3±0.2, 4.8±0.2, 9.5±0.2, 13.0±0.2, 20.0±0.2 and 28.8±0.2.

2. The polymorphic form APO-I of Ivacaftor of claim 1, wherein the powder x-ray diffractogram further comprises at least one peak, in terms of 2-theta degrees, selected from the group consisting of: 9.0±0.2, 12.0±0.2, 14.8±0.2, 16.1±0.2, 21.7±0.2 and 27.9±0.2.

3. The polymorphic form APO-I of Ivacaftor of claim 1, having a DSC thermogram having endothermic peaks at about 240.8° C. and about 315.8° C. and an exothermic peak at about 245.9° C.

4. A process for the preparation of a polymorphic form APO-I of Ivacaftor of claim 1, wherein the process comprises the following steps:
    (a) adding an Ivacaftor solvate to an organic solvent or a mixture of organic solvents selected from the group consisting of methanol, ethanol, propanol, isopropanol, butanol, toluene, xylene, hexane and heptane, thereby forming a reaction mixture;
    (b) maintaining the reaction mixture at a temperature range of from about 0° C. to about 30° C.; and
    (c) isolating the polymorphic form APO-I of Ivacaftor.

5. The process of claim 4, wherein the Ivacaftor solvate is a solvate with methanol, ethanol, methyl ethyl ketone, isopropyl acetate, acetonitrile, methyl isobutyl ketone or water.

6. The process of claim 4, wherein the Ivacaftor solvate is a methyl isobutyl ketone solvate of Ivacaftor.

7. The process of claim 4, wherein the organic solvent is methanol, ethanol, propanol, isopropanol, butanol, toluene, xylene, hexane, heptane or a mixture thereof.

8. The process of claim 7, wherein the organic solvent is a mixture of toluene and methanol and wherein the volume ratio of toluene to methanol in the mixture is in the range of from about 1 to 1 to about 1 to 10.

9. A pharmaceutical composition comprising the polymorphic form APO-I of Ivacaftor of claim 1 with one or more pharmaceutically acceptable carriers.

\* \* \* \* \*

UNITED STATES PATENT AND TRADEMARK OFFICE
CERTIFICATE OF CORRECTION

PATENT NO. : 9,809,551 B2
APPLICATION NO. : 15/036137
DATED : November 7, 2017
INVENTOR(S) : Padiyath Mohammed Akbarali et al.

Page 1 of 1

It is certified that error appears in the above-identified patent and that said Letters Patent is hereby corrected as shown below:

On the Title Page

Column 2, Primary Examiner, Line 1, delete "Vankataraman Balasubramanian" and insert
-- Venkataraman Balasubramanian --

In the Specification

Column 1, Line 10, delete "Nov. 13, 2013," and insert -- Nov. 13, 2014, --

Signed and Sealed this
Twentieth Day of February, 2018

Andrei Iancu
*Director of the United States Patent and Trademark Office*